United States Patent [19]

Bell

[11] 4,347,362

[45] Aug. 31, 1982

[54] 1-ALKYL-4-AMINO-3-(3-AMINOTRIAZOLO)-1,8 NAPHTHYRIDINE-2-ONES

[75] Inventor: Stanley C. Bell, Narberth, Pa.

[73] Assignee: American Home Products Corporation, New York, N.Y.

[21] Appl. No.: 309,630

[22] Filed: Oct. 8, 1981

[51] Int. Cl.³ .......................................... C07D 471/04
[52] U.S. Cl. .................................... 546/123; 424/256
[58] Field of Search ........................................ 546/123

[56] References Cited

U.S. PATENT DOCUMENTS 4,128,649 12/1978 Hardtmann ......................... 546/123
4,176,183 11/1979 Baldwin et al. ..................... 546/123

OTHER PUBLICATIONS

Chemical Abstracts, vol. 94, (1981), 175095c.

*Primary Examiner*—Norma S. Milestone
*Attorney, Agent, or Firm*—George Tarnowski

[57] ABSTRACT

1-alkyl-4-amino-3-(3-aminotriazolo)-1,8-naphthyridine-2-ones are antihypertensive agents.

2 Claims, No Drawings

1-ALKYL-4-AMINO-3-(3-AMINOTRIAZOLO)-1,8 NAPHTHYRIDINE-2-ONES

BRIEF DESCRIPTION OF THE INVENTION

In accordance with this invention there are provided 4-amino-3-(3-aminotriazolo)-1,8-naphthyridine-2-ones which act as antihypertensive agents.

DETAILED DESCRIPTION OF THE INVENTION

The anti-hypertensive agents of this invention are compounds of the formula:

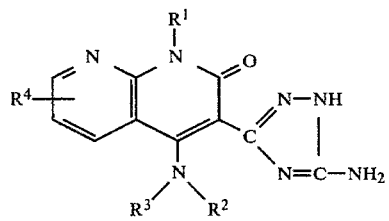

in which
$R^1$ is hydrogen or alkyl of 1 to 6 carbon atoms; and
$R^2$ and $R^3$ are independently, hydrogen or alkyl of 1 to 6 carbon atoms;
$R^4$ is hydrogen or alkyl of 1 to 6 carbon atoms;
or a pharmaceutically acceptable salt thereof.

The compounds of the invention are capable of forming acid addition salts. It is intended throughout this specification and claims to embrace the pharmaceutically acceptable salts of such compounds, which salts are conveniently derived from such acids as hydrochloric hydrobromic, sulfuric, phosphoric, methane sulfonic, nitric, p-toluene sulfonic, acetic, citric, maleic, succinic acid and the like.

The intermediate 4-halo-naphthyridine precursors for production of the anti-secretory agents of this invention are compounds of the formula:

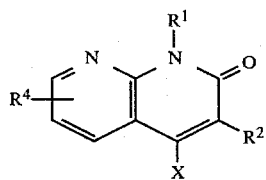

in which
$R^1$ is hydrogen, alkyl of 1 to 6 carbon atoms;
$R^2$ is $-CO_2R^5$ where $R^5$ is alkyl of 1 to 6 carbon atoms;
$R^4$ is hydrogen or alkyl of 1 to 6 carbon atoms; and
X is chloro, bromo, or iodo.

The 4-amino-3-(3-aminotriazolo)-1,8-naphthyridine-2-ones of this invention are prepared by a process which begins by preparing a 4-amino-3-carboxy-1,2-dihydro-2-oxo-1,8-naphthyridine obtained by reacting a primary or secondary amine with an appropriately substituted 4-halo-naphthyridine precursor. By 4-halo, applicant intends to embrace the chloro, bromo and iodo derivatives. The 4-halo-naphthyridine precursors are prepared by conventional techniques involving displacement of a 4-hydroxyl group from the corresponding 4-hydroxynaphthyridine with such halogenating reagents as thionyl chloride to obtain the 4-chloro-naphthyridines and phosphorus oxybromide to obtain the 4-bromo-naphthyridines. The 4-iodo-naphthyridines are prepared by reaction of a 4-chloro-naphthyridine with sodium iodide in an appropriate inert solvent such as acetone.

Alternatively, the 4-chloro, bromo or iodo-naphthyridines may also be prepared directly by nitrosation of the appropriately ring substituted 4-amino-naphthyridines in hydrochloric, hydrobromic or hydroiodic acid, respectively.

The 4-amino-3-carboxy-1,2-dihydro-2-oxo-1,8-naphthyridine can also be prepared directly from a 2-substituted amino nicotinonitrile reacting with a lower alkyl malonyl chloride followed by a Dieckman ring closure with sodium alkoxide, or an analogous strong base such as potassium alkoxide or NaH or $NaNH_2$ in an aprotic solvent, thusly:

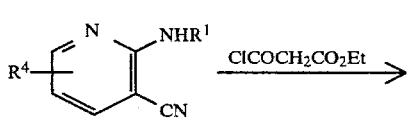

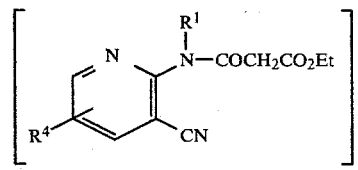

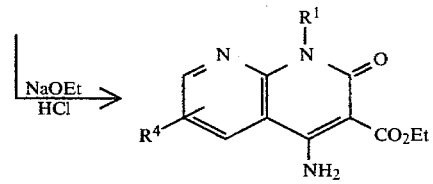

Alternatively, the 2-substituted aminonicotinonitrile may be reacted with the sodio salt of a di-lower alkyl malonate to give directly on acidification a 4-amino-3-carboxy-1,2-dihydro-2-oxo-1,8-naphthyridine derivative, thusly:

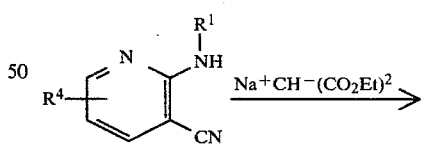

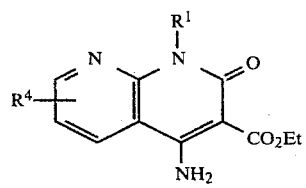

where $R^1$ in the preceding equation is hydrogen, the product may be treated with a lower alkali metal alkoxide and alkylated with a lower alkyl, iodide, bromide or chloride (RX where R contains 1 to 6 carbon atoms) to afford the 1-alkyl-4-amino-3-carboxy-1,2-dihydro-2-oxo-1,8-naphthyridine derivatives described above.

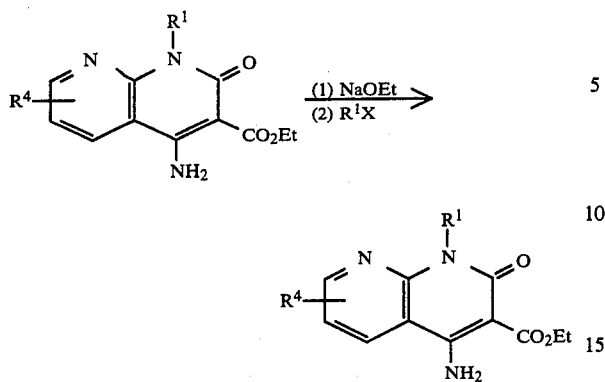

The 3-aminotriazolo substituent, which can exist in three tautomeric forms:

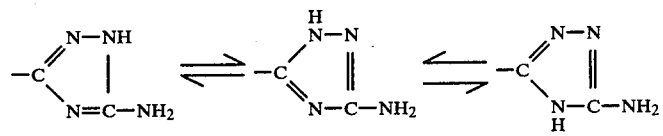

is readily produced at 3-position of the 4-amino and 4-substituted amino-3-alkoxy-carbonyl-1,8-naphthyridine derivatives by reaction of the ester —$CO_2R^5$ with amino guanidine in an organic solvent solution.

When employed to lower blood pressures, the effective dosage of the substance active for such treatment will vary according to the particular compound being employed, the severity and nature of condition being treated. Therapy should be initiated at low doses, the dosage thereafter being increased, if necessary, to produce the desired anti-hypertensive effect.

Further, when employed as anti-hypertensive agents, the compounds of the invention, or pharmacologically acceptable acid addition salts thereof, may be administered alone or in combination with pharmaceutically acceptable carriers, so that the compounds of this invention may be administered by conventional oral or parenteral routes as solids, liquids, or isotonic solutions. The proportion and nature of such carriers would be determined by the solubility and other chemical properties of the compound selected, the chosen route of administration, and standard pharmaceutical practice although it is considered desirable and feasible to use the compounds neat or pure without additives other than for the purpose of providing suitable pharmaceutically acceptable solid or liquid dosage units.

The following examples illustrate the preparation of representative intermediates and final products of the invention and the pharmacological testing of the compounds of the invention.

EXAMPLE 1

4-Amino-1,2-Dihydro-2-Oxo-1,8-Naphthyridine-3-Carboxylic Acid Ethyl Ester

To a solution of 4.14 g (0.18 g. atom) of sodium in 100 ml. of ethanol was added 28.8 g. (0.18 mole) of diethyl malonate. After stirring at room temperature for 5 minutes, 7.14 g. (0.06 mole) of 2-aminonicotinonitrile was added and the mixture was heated under reflux for 6 hours. The mixture was cooled and was diluted with 100 ml. of water and was acidified with conc. hydrochloric acid. On cooling, a precipitate was formed which was collected and was triturated with 1000 ml. of boiling ethanol. The mixture was filtered and the filtrate was cooled in ice to precipitate 2.9 g. of product, m.p. 264°–267° C. dec.

Analysis for: $C_{11}H_{11}N_3O_3$, Calculated: C, 56.65; H, 4.75; N, 18.02, Found: C, 56.37; H, 4.79; N, 18.08.

EXAMPLE 2

4-Amino-1,2-Dihydro-2-Oxo-1,8-Naphthyridine-3-Carboxylic Acid

The material which was insoluble in boiling ethanol from the previous reaction was recrystallized from N,N-dimethylformamide to give a small amount of the corresponding carboxylic acid, m.p. 296°–298° C. dec.

Analysis for: $C_9H_7N_3O_3$, Calculated: C, 52.68; H, 3.44; N, 20.48, Found: C, 52.27; H, 3.72; N, 20.23.

EXAMPLE 3

4-Chloro-1,2-Dihydro-1-Methyl-2-Oxo-1,8-Naphthyridine-3-Carboxylic Acid, Ethyl Ester To 200 ml. of anhydrous N,N-dimethylformamide was added 1.9 g. (0.04 mole) of 50% sodium hydride. Then 6.5 g. (0.04 mole) of 3,4-dihydro-1,3-dioxo-1H-pyrido[2,3-d][1,3]oxazine was added in portions over 5 minutes. After 14.2 g. (0.1 mole) of methyl iodide was added, the mixture was stirred at room temperature for 2 hours. The mixture was cooled and water was slowly added. On further dilution of water, a precipitate was formed which was collected, air dried and was recrystallized from ethanol to give 2.6 g. of 1-methyl-1H-4H-pyrido[2,3-d][1,3]-oxazine-2,4-dione, m.p. 163°–166° C.

Analysis for: $C_8H_6N_2O_3$, Calculated: C, 53.93; H, 3.40; N, 15.73, Found: C, 53.60; H, 3.52; N, 15.87.

To a solution of 0.345 g. (0.15 g. atom) of sodium in 30 ml. of ethanol was added 4.8 g. of diethyl malonate. The mixture was stirred at room temperature for 5 minutes and then was evaporated in a rotary evaporator. The residue was dissolved in 30 ml. of N,N-dimethylformamide and 2.67 g. (0.015 mole) of 1-methyl-1H-4H-pyrido[2,3-d][1,3]-oxazine-2,4-dione was added. The mixture was heated under reflux for 10 minutes and the thick mixture was dissolved in 100 ml. of water. The solution was acidified with conc. hydrochloric acid and the precipitate which formed was collected, air dried, and a small amount of this 1.7 g. was recrystallized from ethanol to give the analytical sample of 4-hydroxy-1,2-dihydro-1-methyl-2-oxo-1,8-naphthyridine-3-carboxylic acid, ethyl ester, m.p. 158°–160° C.

Analysis for: $C_{12}H_{12}N_2O_4$, Calculated: C, 58.06; H, 4.87; N, 11.29, Found: C, 57.86; H, 4.85; N, 11.18.

A stirred mixture of 1.7 g. of 4-hydroxy-1,2-dihydro-1-methyl-2-oxo-1,8-naphthyridine-3-carboxylic acid ethyl ester in 25 ml. of phosphorus oxychloride was heated under reflux for 2 hours. The phosphorus oxychloride was removed in a rotary evaporator and the residue was poured into 100 ml. of ice water. The precipitate which formed was collected, air dried and a small amount of the 1.9 g. was recrystallized from heptane twice to give the analytical sample of the title compound, m.p. 132°–135° C.

Analysis for: $C_{12}H_{11}ClN_2O_3$, Calculated: C, 54.04; H, 4.16; N, 10.51, Found: C, 53.61; H, 4.16; N, 10.51.

By analogous procedures, the intermediates for amine introduction in 4-position useful in the preparation of the variously substituted compounds of this invention are readily obtained. Likewise, the initial pyrido-oxazine reactant may be alkylated with alkyl iodides of 1 to 6 carbon atoms to afford the corresponding 1-substituted precursors.

EXAMPLE 4

4-Amino-1,2-Dihydro-1-Methyl-2-Oxo-1,8-Naphthyridine-3-Carboxylic Acid Ethyl Ester To a solution of 2.66 g. (0.02 mole) of 2-methylaminonicotinonitrile in 100 ml. of anhydrous ethyl ether was added 1.5 g. (0.01 mole) of ethyl malonyl chloride. After stirring at room temperature for 1 hour, the mixture was filtered. The filtrate was evaporated in a rotary evaporator and the residue was dissolved in 10 ml. of ethanol. This solution was added to a solution of 0.46 g. (0.02 g. atom) of sodium in 50 ml. of ethanol. After stirring for 5 minutes, the mixture was diluted with water and was acidified with conc. hydrochloric acid. The precipitate which formed was collected, air dried and was recrystallized from ethanol to afford 0.9 g. of product, m.p. 203°–206° C.

Analysis for: $C_{12}H_{13}N_3O_3$, Calculated: C, 58.29; H, 4.30; N, 17.00, Found: C, 57.96; H, 5.31; N, 17.16.

EXAMPLE 5

4-Amino-1-Ethyl-1,2-Dihydro-2-Oxo-1,8-Naphthyridine-3-Carboxylic Acid Ethyl Ester Following the procedure of Taylor et al., J. Org. Chem., 19, 1633 (1954), a stirred mixture of 14 g. of nicotinamide N-oxide, 29.7 g. of phosphorus pentachloride and 40 ml. of phosphorus oxychloride was heated under reflux for 2 hours. The phosphorus oxychloride was evaporated in a rotary evaporator and the residue was poured over ice. The insoluble material was collected, air dried and was recrystallized from heptane to give 6.0 g. of 2-chloronicotinonitrile.

A stirred mixture of 4 g. of 2-chloronicotinonitrile in 200 ml. of a saturated ethanolic ethylamine solution was heated under reflux for 5 hours. The solution was cooled and was diluted with 400 ml. of water. The precipitate of 2-ethylaminonicotinonitrile which formed was collected, air dried and was used directly in the next step without further purification.

To a solution of 4.4 g. (0.03 mole) of 2-ethylaminonicotinonitrile in 200 ml. of anhydrous diethyl ether was added 2.25 g. (0.015 mole) of ethyl malonyl chloride. After stirring at room temperature for 2 hours, the mixture was filtered. The filtrate was evaporated in a rotary evaporator and the residue was dissolved in 20 ml. of ethanol. This solution was added to a solution of 0.69 g. (0.03 g. atom) of sodium in 100 ml. of ethanol. After stirring for 5 minutes at room temperature, the mixture was diluted with water and was acidified with conc. hydrochloric acid. The precipitate which formed was collected, air dried and was recrystallized from ethyl acetate to afford 1.8 g. of the title compound as a hemihydrate, m.p. 205°–208° C.

Alternatively, 4-Amino-1-ethyl-1,2-dihydro-2-oxo-1,8-naphthyridine-3-carboxylic acid ethyl ester may be prepared as follows:

To a solution of 2.07 g. (0.09 g. atom) of sodium in 75 ml. of absolute ethanol was added 14.4 g. (0.09 mole) of diethyl malonate. The solution was stirred at room temperature for 5 minutes. The 4.4 g. (0.03 mole) of 2-ethylaminonicotinonitrile was added and the mixture was heated under reflux for 6 hours. The mixture was cooled and was diluted with 75 ml. of water and was acidified with concentrated hydrochloric acid. The precipitate which formed was collected and was dried to give 3.2 g. of material. Two recrystallizations from ethanol provided 1.1 g. of pure product, m.p. 203°–207° C.

A third method of preparing 4-amino-1-ethyl-1,2-dihydro-2-oxo-1,8-naphthyridine-3-carboxylic acid ethyl ester is as follows:

To a stirred solution of 0.026 mole of sodium ethoxide (0.6 g. sodium in 200 ml. of ethanol) was added 6 g. (0.025 mole) of 4-amino-1,2-dihydro-2-oxo-1,8-naphthyridine-3-carboxylic acid ethyl ester and 11.7 g. (0.075 mole) of ethyl iodide. The reaction mixture was heated under reflux for 4 hours; then filtered. The filtrate was taken to dryness and the residue was washed with water. The crude product amounted to 2.3 g., m.p. 194°–198° and gave no melting point depression on admixture with samples prepared as previously described.

Analysis for: $C_{13}H_{15}N_3O_3$ ½$H_2O$, Calculated: C, 57.77; H, 5.97; N, 15.55, Found: C, 57.82; H, 5.97; N, 15.81.

EXAMPLE 6

4-Amino-1-Ethyl-1,2-Dihydro-2-Oxo-1,8-Naphthyridine-3-Carboxylic Acid, n-Butyl Ester To a solution of 1.38 g. (0.06 g. atom) of sodium in 200 ml. of n-butyl alcohol was added 12.96 g. (0.06 mole) of di-n-butylmalonate. After stirring for 2 minutes, 8.82 g. (0.06 mole) of 2-ethylaminonicotinonitrile was added. The mixture was heated under reflux for 5 hours. The n-butyl alcohol was removed in a rotary evaporator and the residue was triturated with 250 ml. of a 20% aqueous hydrochloric acid solution. This mixture was extracted with 200 ml. of ethyl ether. The ether layer was dried over magnesium sulfate, filtered and the ether layer was acidified with an ethereal hydrochloric acid solution. The precipitate which formed was collected and this material was triturated with 100 ml. of a 10% aqueous sodium carbonate solution. The insoluble material was dissolved in ether. The ether layer was dried over magnesium sulfate, filtered and the ether was evaporated. The residue was recrystallized from ethyl acetate to afford 0.5 g. of product, m.p. 117°–120° C.

Analysis for: $C_{15}H_{19}N_3O_3$, Calculated: C, 62.26; H, 6.62; N, 14.52, Found: C, 61.96; H, 6.50; N, 14.74.

EXAMPLE 7

4-Amino-1-Propyl-1,2-Dihydro-2-Oxo-1,8-Naphthyridine-3-Carboxylic Acid Ethyl Ester A stirred mixture of 2.76 g. (0.02 mole) of 2-chloronicotinonitrile prepared as in Example 9, 1.18 g. (0.02 mole) of propylamine and 2.12 g. (0.02 mole) of sodium carbonate in 25 ml. of ethanol was heated under reflux for 5 hours. The mixture was filtered and the filtrate was cooled in ice and was diluted with water to the cloudy point. The precipitate which formed was collected, air dried and was recrystallized three times from pentane to give 0.7 g. of 2-propylaminonicotinonitrile, m.p. 33°–35° C. which was used directly in the next step.

To a solution of 4.5 g. (0.028 mole) of 2-propylaminonicotinonitrile in 100 ml. of anhydrous diethyl ether was added 2.1 g. (0.014 mole) of ethyl malonyl chloride. The mixture was stirred at room temperature for 2 hours and was filtered. The filtrate was evaporated in a rotary evaporator and the residue was dissolved in 10 ml. of ethanol. This solution was added to a solution of 0.64 g. (0.028 g. atom) of sodium in 50 ml. of ethanol. After stirring for 10 minutes, the mixture was diluted with water and was acidified with conc. hydrochloric acid. The precipitate which formed was collected, air dried and was recrystallized from ethyl acetate to give 2.1 g. of the title compound, m.p. 165°–168° C.

Analysis for: $C_{14}H_{17}N_3O_3$, Calculated: C, 61.08; H, 6.22; N, 15.26, Found: C, 61.02; H, 6.04; N, 15.19.

EXAMPLE 8

4-Amino-1-Isobutyl-1,2-Dihydro-2-Oxo-1,8-Naphthyridine-3-Carboxylic Acid Ethyl Ester A stirred mixture of 5 g. of 2-chloronicotinonitrile in 25 ml. of isobutylamine was heated under reflux for 30 minutes. The mixture was cooled and was diluted with water to the cloudy point. The precipitate which formed was collected, air dried and was recrystallized from heptane to give 4 g. of 2-isobutylaminonicotinonitrile, m.p. 80°–84° C.

Analysis for: $C_{10}H_{13}N_3$, Calculated: C, 68.54; H, 7.48; N, 23.98, Found: C, 68.93; H, 7.77; N, 24.24.

To a solution of 12.25 g (0.07 mole) of 2-isobutylaminonicotinonitrile in 300 ml. of anhydrous ethyl ether was added 5.2 g. (0.035 mole) of ethyl malonyl chloride. The mixture was stirred at room temperature for 30 minutes and was filtered. The filtrate was evaporated in a rotary evaporator and the residue was dissolved in 20 ml. of ethanol. This solution was added to a solution of 1.6 g. of sodium in 150 ml. of ethanol. After stirring at room temperature for 5 minutes, the mixture was diluted with water and was acidified with conc. hydrochloric acid. The precipitate which formed was collected, air dried and was recrystallized from ethyl acetate to afford 2.1 g. of the title product, m.p. 157°–159° C.

Analysis for: $C_{15}H_{19}N_3O_3$, Calculated: C, 62.26; H, 6.62; N, 14.52, Found: C, 62.03; H, 6.55; N, 14.56.

EXAMPLE 9

4-Amino-3-(3-Amino-1H-1,2,4-Triazol-5-yl)-1-ethyl-1,8-naphthyridine-2(1H)-one, hydrochloride To a solution of 5.8 g. (0.105 m) of sodium methoxide in 200 ml. of ethanol is added with stirring 15.1 g (0.11 m) of amino guanidine nitrate. After five minutes, 7.8 g (0.03 m) of 4-amino-1-ethyl-1,2-dihydro-2-oxo-1,8-naphthyridine-3-carboxylic acid ethyl ester, prepared according to Example 5, is added to the reaction mixture and it is stirred at room temperature for 4 days. The solid is filtered off, washed with ethanol, suspended in 200 ml. of water and filtered. Yield: 4.6 g.; m.p. >300. This solid is suspended in about 50 ml. of warm water and dilute hydrochloric acid is added. The solid dissolves and is filtered from impurities. Addition of excess concentrated hydrochloric acid causes the hydrochloride salt to precipitate out. It is filtered (2.9 g.), suspended in methanol and filtered again as a white solid. It is dried in vacuo at 100° C. for analysis.

Analysis for: $C_{12}H_{13}N_7O$ HCl (MW 307.74), Calculated: C, 46.84; H, 4.59; N, 31.86, Found: C, 46.59; H, 4.59; N, 32.03.

EXAMPLE 10

The compounds of the invention are effective in lowering blood pressures as shown in standard tests using hypertensive rats. Such tests are conducted on spontaneously or surgically hypertensive rats. Test groups and control groups usually consist of 4–6 rats, and the test compounds and reference compounds are administered either orally or intraperotoneally. Systolic blood pressures are measured by an indirect technique using the Decker Caudal Plethysmograph or other appropriate sensor, and readings are taken prior to drug administration and periodically thereafter, for example at 1.5, 4, and 24 hours after administration. Results are analyzed statistically. Reference compounds used include clonidine, hydralazine, guanethidine, methyldopa, and reserpine.

When administered in doses of 5–50 mg/kg., the compounds of the invention demonstrate moderate to marked abilities to reduce blood pressures. The antihypertensive activity of a compound is rated as follows:

| Activity | Systolic Decrease In Blood Pressure |
|---|---|
| Not Significant (NS) | <15 mm. Hg. |
| Borderline (BDL) | 15–25 |
| Slight (SLT) | 25–35 |
| Moderate (MOD) | 25–50 |
| Marked (MKD) | over 50 |

When tested in spontaneously hypertensive rats as described above, the below cited compound gave the following results:

| Compound | Dose (mg/kg) | Activity |
|---|---|---|
| 4-amino-3-(5-amino-(1H)-1,2,4-triazol-3-yl)-1-ethyl-1,8-naphthyridin-2(1H)-one, hydrochloride | 50 | MKD at 1.5 and 4 hr. |
| | 25 | MKD at 1.5 and 4 hr. |
| | 10 | MKD at 1.5 and 4 hr. |
| | 5 | MOD at 1.5 hr |

What is claimed is:

1. A compound of the formula:

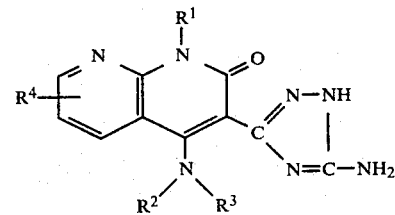

in which
R$^1$ is hydrogen or alkyl of 1 to 6 carbon atoms; and
R$^2$ and R$^3$ are independently hydrogen or alkyl of 1 to 6 carbon atoms;
R$^4$ is hydrogen or alkyl of 1 to 6 carbon atoms;
or a pharmaceutically acceptable salt thereof.

2. The compound of claim 1, having the name 4-amino-3-(3-amino-1H-1,2,4-triazol-5-yl)-1-ethyl-1,8-naphthyridin-2(1H)-one.

* * * * *